(12) United States Patent
Huang et al.

(10) Patent No.: US 10,561,692 B2
(45) Date of Patent: Feb. 18, 2020

(54) ALLERGY-INHIBITING SEA GRAPE EXTRACT, ITS PREPARATION METHOD AND APPLICATION THEREOF

(71) Applicants: Teh Fong Min International Co., Ltd., Taipei (TW); East Green BIO Corporation, Hualien, Hualien County (TW)

(72) Inventors: Yu-Lin Huang, Taipei (TW); Huey-Min Lai, Hsinchu (TW); Tsung-Han Lee, Kaohsiung (TW); Wei-Yung Hsieh, Taipei (TW); Xiu-Ci Shen, Taipei (TW); Tseng-Peng Li, Taipei (TW)

(73) Assignee: TEH FONG MIN INTERNATIONAL CO., LTD., Taipei (TW)

( * ) Notice: Subject to any disclaimer, the term of this patent is extended or adjusted under 35 U.S.C. 154(b) by 898 days.

(21) Appl. No.: 15/003,342

(22) Filed: Jan. 21, 2016

(65) Prior Publication Data

US 2017/0209507 A1      Jul. 27, 2017

(51) Int. Cl.
*A61K 36/05* (2006.01)

(52) U.S. Cl.
CPC .......... *A61K 36/05* (2013.01); *A23V 2002/00* (2013.01)

(58) Field of Classification Search
None
See application file for complete search history.

(56) References Cited

FOREIGN PATENT DOCUMENTS

| KR | 10-1252149 B1 | 4/2013 |
|---|---|---|
| TW | I484966 B | 5/2015 |

OTHER PUBLICATIONS

English translation of JP2005139074A provided by JPO website. (Year: 2005).*
English translation of JP2011012052A provided by JPO website. (Year: 2011).*

* cited by examiner

*Primary Examiner* — Michael Barker
(74) *Attorney, Agent, or Firm* — Muncy, Geissler, Olds & Lowe, P.C.

(57) ABSTRACT

Present invention relates to an allergy-inhibiting sea grape extract, its preparation method and thereof. The preparation method includes following steps: the sea grape is blended in distilled water in the weight ratio of 1:1~20, mix thoroughly, stir at 20~100° C. for 30~120 minutes. The fluid obtained after the first filtration is the sea grape extract. The sea grape extract can be subjected to the second filtration by using EW, PW and DK membranes and freeze-dried to give a refined sea grape extract. The invention exhibits superior allergy-inhibiting effect; moreover, the prepared extract does not cause allergy and can be used in cosmetics and food.

6 Claims, 3 Drawing Sheets

ALLERGY-INHIBITING SEA GRAPE EXTRACT, ITS PREPARATION METHOD AND APPLICATION THEREOF

BACKGROUND OF THE INVENTION

1. Field of the Invention

Present invention relates to a sea grape extract, in particular, a method for preparation of a sea grape extract which can inhibit allergy and does not cause allergic reactions and its applications thereof.

2. Description of the Prior Art

Allergy is a dysfunction of the immune system, an over-reaction to some environmental substance (also called an allergen). After entering the body, the allergen binds to IgE Ab and subsequently triggers release of the inflammatory substances from mast cells, such as histamine, resulting in inflammatory responses in various tissues. The symptoms of allergy vary with the tissues that release histamine, including runny nose, watery eyes, itching, shortness of breath and dry skin, even life-threatening shock in severe cases. Drugs such as antihistamines are usually used to treat allergies in allergy-prone people, but nearly all anti-allergy medications have certain side effects. Therefore, using natural plants or allergy-inhibiting ingredients extracted from plants to inhibit the allergic activity is also an issue of public concern.

Sea grape belongs to green algae, contains not only rich seaweed polysaccharides but also low fat and low calorie. In addition, with its caviar-like crisp taste, sea grape is the best natural health food for many Japanese and experts and also a high-class ingredient for Japanese cuisine. Moreover, sea grape contains vast amount of trace elements which have the anti-aging effect. As a result, sea grape extract has been listed as a legitimate ingredient for use in cosmetics by the World Cosmetic Society.

In the past, the technology for sea grape extraction usually uses alcohol or other organic solvents for extraction. The Taiwan patent 1484966 discloses an extraction method for sea grape extraction which uses alcohol for crude extraction of the sea grape powder, followed by separation of the active substance(s) by using n-hexane and ethyl acetate. The extracted substance has anti-cancer activity. In the Korea patent KR101252149, water and C1-C4 alcohols are used to prepare a sea grape extract and said extract has anti-oxidative, anti-inflammatory and moisturizing effects. All of the sea grape extracts obtained by prior arts showed no allergy-inhibiting effect; moreover, using organic solvents for sea grape extraction will leave residual organic solvents which may be harmful to the body.

Most of the technologies mentioned in prior arts use organic solvents for sea grape extraction. Certain residual organic solvents are health hazards. Because the polarity of each solvent is different, the extraction ability also varies. Under the premise of no use of organic solvents, how to extract a sea grape extract that can inhibit allergy is an important task of present invention.

SUMMARY OF THE INVENTION

In view of the deficiencies of prior technology, the inventor hopes, without using any organic solvent, to provide a natural and safe sea grape extract by using water for extraction at a specific temperature for a specified time period and followed by membrane filtration to acquire the allergy-inhibiting active substance(s) of the sea grape.

In one aspect, present invention provides an extraction method for extracting sea grape extract, which comprises the following steps:

Step 1: blend sea grape in distilled water, wherein the weight ratio of sea grape to water is 1:1~20, mix thoroughly to give a sea grape paste;

Step 2: continuous stirring of the sea grape paste at a stirring temperature of 20~100° C. for 30~120 min;

Step 3: the fluid obtained after first filtration is the sea grape extract.

According to the invention, in step 1, the sea grape may be fresh sea grape, dried sea grape, or sea grape powder.

According to the invention, in step 2, the stirring temperature is 60~90° C.; preferably, the stirring temperature is 85° C.; the stirring time is 60~105 minutes; preferably, the stirring time is 90 minutes.

According to the invention, in step 3, the conditions for first filtration are 5 microns and 1 micron.

According to the invention, a second filtration may be conducted after the first filtration and said second filtration is membrane filtration; the first membrane used in said membrane filtration is the EW membrane made by GE, the second membrane used is the PW membrane made by GE and the third membrane used is the DK membrane made by GE.

In another aspect, present invention provides an allergy-inhibiting sea grape extract which is obtained by using the abovementioned extraction method for sea grape extraction.

In the other aspect, present invention provides a composition, comprising an allergy-inhibiting sea grape extract at an effective level, and a cosmetically acceptable, edible, or pharmaceutically acceptable excipient, wherein the composition is a cosmetic composition, food composition, or a pharmaceutical composition.

According to the invention, the effective amount of said sea grape extract is 1 mg/ml and above; preferably, the effective amount of said sea grape extract is 4 mg/ml.

According to the invention, the form of the cosmetic composition is selected from the following compositions: creams, multiple emulsions, anhydrous compositions, aqueous dispersions, oils, emulsions, balm, foams, lotions, gels, emulsions, aqueous ethanol solution, hydroglycolic solution, hydrogels, coating poultices, slurries, soaps, shampoo, conditioner, clear slurry, ointment, mousse, hair cream, powders, bars, pencils, sprays, aerosols, capsules, gelatin capsules, soft capsules, hard capsules, tablets, dragees, granules, chewing gum, solutions, suspensions, emulsions, syrups, polysaccharides films, jellies and gelatin.

According to the invention, the cosmetic composition may be mixed with products including eye cream, foundation, washing foam (cream), make-up remover, eye shadow, lipstick, lip gloss, lip balm and powder.

According to the invention, the ingredients of the shampoo are surfactant 10~50%, emollient 0.3~2%, sea grape extract 0.01~0.1%, thickener 0~2%, fragrance 0.1~1%, preservative 0.3~1% and water.

DETAILED DESCRIPTION OF THE PREFERRED EMBODIMENT

All technical and scientific terms used in the invention, unless otherwise specified, have the common meanings that are understood by person skilled in the art. The foregoing detailed description of the invention and the specific examples are provided herein for the purpose of illustration only, and the invention is not limited to the preferred embodiments shown. It should be understood that any changes or modifications within the spirit of the invention shall be included in the scope of present invention.

Example 1

1. Preparation Method for Sea Grape Extract (I)

Take 80 g of the dried powder of sea grape and 1,600 g of distilled water, the sea grape used is *Caulerpa lentillifera*, blend thoroughly (the temperature is 85° C., the time is 90 minutes), followed by filtration using 5-μm and 1-μm filter membranes to give the fluid of sea grape extract (I); the obtained fluid is then subjected to the second filtration; the first membrane is the EW membrane made by GE and microfiltration eliminates large particles; the second membrane is the PW membrane made by GE and ultrafiltration eliminates tiny particles; the third membrane is the DK membrane made by GE and nanofiltration eliminates salts; the filtrate is then freeze-dried after filtration to give the sea grape extract (I). The abovementioned *Caulerpa lentillifera* may be replaced by other species of sea grapes such as *Caulerpa taxifolia*.

2. The Sea Grape Extract (I) does not Trigger Allergy

Figure 1:
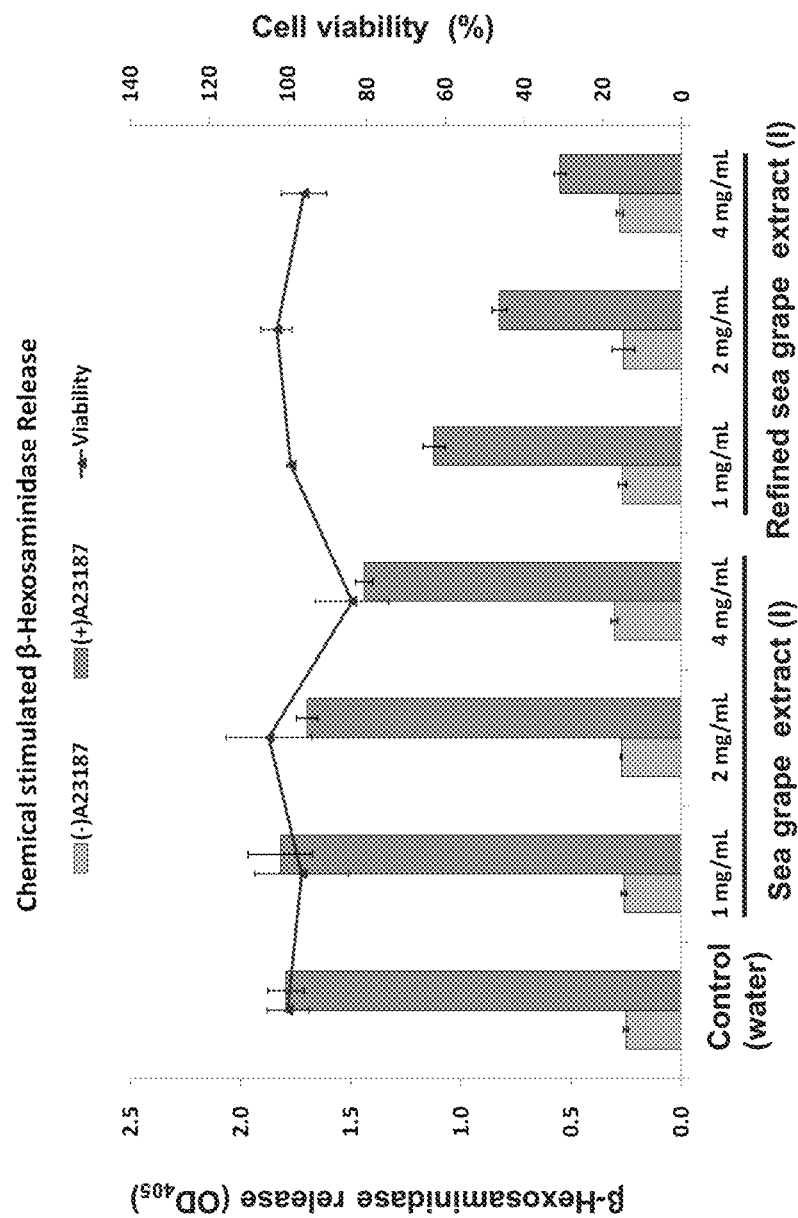
FIG. 1 shows the allergy-inducing responses. Calcium ionophore A23187 stimulates degranulation of cells to release β-hexosaminidase, the effect of sea grape extract on the amount of released β-hexosaminidase.

Release of the allergic mediator, β-hexosaminidase, of the cells treated with only sea grape extract (I) or refined sea grape extract (I) in the absence of the stimulant (A23187(−)) (FIG. 1). Comparisons of the sea grape extract (I) alone group, refined sea grape (I) alone group and the control group. Use of the sea grape extract (I) alone and the refined sea grape (I) alone did not increase the release of β-hexosaminidase, suggesting the sea grape extract (I) and refined sea grape (I) do not trigger allergy.

3. Experiment of Allergy Induction

Calcium ionophore A23187 stimulates degranulation of cells to release the allergic mediator, β-hexosaminidase, the concentration of β-hexosaminidase is determined by enzyme-linked immunosorbent assay (ELISA). From the Ctr results of FIG. 1, Calcium ionophore A23187 induces release of β-hexosaminidase.

4. The Sea Grape Extract (I) Inhibits Allergy

Figure 2:
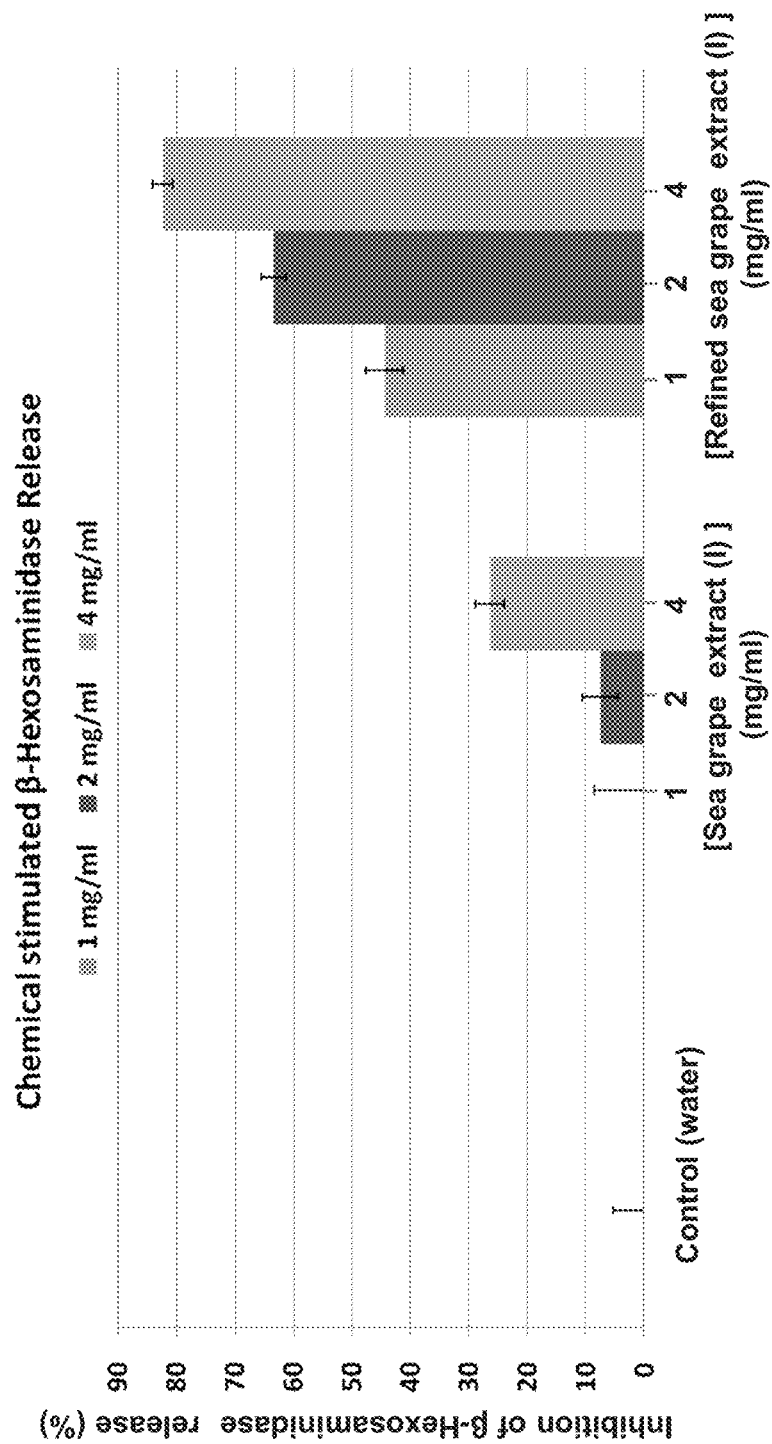
FIG. 2 shows the allergy-inhibiting effect of sea grape extract.

According to the results of FIG. 2, the sea grape extract (I) can inhibit release of β-hexosaminidase induced by calcium ionophore A23187 (A23187(+) group), 2 mg/ml of the sea grape extract (I) showed 8% reduction of the released β-hexosaminidase and 4 mg/ml of the sea grape extract (I) showed 25% reduction of the released β-hexosaminidase; the β-hexosaminidase inhibition effect of refined sea grape extract (I) is more significant, the refined sea grape extract (I) at 1 mg/ml inhibited 45% of β-hexosaminidase release, 4 mg/ml of the refined sea grape extract (I) inhibited 82% of β-hexosaminidase release without affecting cell viability (FIG. 1).

5. Cosmetic Application of the Refined Sea Grape Extract (I)

Specific amount of distilled water is boiled to 50~60° C. before addition of surfactant, mixed thoroughly. The emollient is added, mix thoroughly. Stop heating. Cool to 30° C. before addition of the refined sea grape extract (I), orange *Citrus sinensis*, sodium anisate, mixed thoroughly to give the shampoo mousse containing the refined sea grape extract (I). The formula of the shampoo mousse is shown in Table 1.

TABLE 1

Formula of the shampoo mousse containing the refined sea grape extract (I)

|  |  |  |
|---|---|---|
| Surfactant | Decyl Glucoside | 5.5% |
|  | Disodium Cocoyl Glutamate | 6% |
|  | Sodium Cocoyl Glutamate | 6% |
|  | Coco-glucoside | 2% |
| Emollient | Glyceryl Oleate | 1% |
|  | Glyceryl Caprylate | 1% |
|  | Glycerin | 1% |
|  | Glyceryl Undecylenate | 0.5% |
| Allergy-inhibiting agent | Sea grape extract (I) | 0.02% |
| Fragrance | Orange *Citrus sinensis* | 0.3% |
| Preservative | Sodium Anisate | 0.5% |
| Solvent | water | Make up to 100% |

6. The Clinical Trial of Cosmetics Containing the Sea Grape Extract (I)

The AMA Laboratories Inc. certified by the Food and Drug Administration (FDA) of the U.S. was retained to conduct the clinical trial to assess skin irritation and sensitivity of the shampoo mousse (the formula is shown in Table 1) containing the refined sea grape extract (I), the number of subjects enrolled is 52, the number of subjects who completed the trial is 50, the subjects were aged 20-68 years, and the gender as well as race are shown in Table 2.

TABLE 2

Subjects enrolled in the clinical trial of the shampoo mousse containing the sea grape extract (I) Statistical data

|  |  |  |
|---|---|---|
| Number of subjects enrolled |  | 52 |
| Number of subjects completing study |  | 50 |
| Age Range |  | 20-68 |
| Sex | Male | 11 |
|  | Female | 41 |
| Race | Caucasian | 41 |
|  | Hispanic | 10 |
|  | Asian | 1 |

The procedure of the clinical trial: the shampoo mousse of Table 1 was diluted 10 fold in water). 0.2 ml of the diluted shampoo mousse sample onto the semi-occlusive, hypoallergenic patch. The patch is then applied directly to the skin of the infrascapulart regions of the back, to the right or left of the midline and the subject is dismissed with instructions not to wet or expose the test area to direct sunlight. After 24 hours the patch is removed by the subjects at home. The procedure is repeated until a series of nine consecutive 24 hour exposures have been made for every Monday, Wednesday, and Friday for three consecutive weeks. In the event of an adverse reaction, the area of erythema and edema is measured. As shown in Table 3, a total of 50 subjects had completed the study. All subjects had no allergic reaction to the shampoo mousse containing refined sea grape extract (I), indicating the shampoo mousse containing refined sea grape extract (I) causes no skin irritation and no allergy.

TABLE 3

Results of the clinical trial of the shampoo mousse containing sea grape extract (I)

| Subject | | | | Response | | | | | | | | | Chall. | |
|---|---|---|---|---|---|---|---|---|---|---|---|---|---|---|
| No. | ID | RACE | SEX | 1 | 2 | 3 | 4 | 5 | 6 | 7 | 8 | 9 | 24 hr | 48 hr |
| 1 | 00 0002 | C | F | 0 | 0 | 0 | 0 | 0 | 0 | 0 | 0 | 0 | 0 | 0 |
| 2 | 27 8204 | H | M | 0 | 0 | 0 | 0 | 0 | 0 | 0 | 0 | 0 | 0 | 0 |
| 3 | 32 9523 | C | M | 0 | 0 | 0 | 0 | 0 | 0 | 0 | 0 | 0 | 0 | 0 |
| 4 | 38 5937 | H | F | 0 | 0 | 0 | 0 | 0 | 0 | 0 | 0 | 0 | 0 | 0 |
| 5 | 38 8908 | C | F | 0 | 0 | 0 | 0 | 0 | 0 | 0 | 0 | 0 | 0 | 0 |
| 6 | 38 9739 | C | M | 0 | 0 | 0 | 0 | 0 | Dc | Dc | Dc | Dc | Dc | Dc |
| 7 | 40 0533 | C | F | 0 | 0 | 0 | 0 | 0 | 0 | 0 | 0 | 0 | 0 | 0 |
| 8 | 40 1523 | C | F | 0 | 0 | 0 | 0 | 0 | 0 | 0 | 0 | 0 | 0 | 0 |
| 9 | 40 3984 | C | F | 0 | 0 | 0 | 0 | 0 | 0 | 0 | 0 | 0 | 0 | 0 |
| 10 | 42 5472 | C | F | 0 | 0 | 0 | 0 | 0 | 0 | 0 | 0 | 0 | 0 | 0 |
| 11 | 44 3503 | C | F | 0 | 0 | 0 | 0 | 0 | 0 | 0 | 0 | 0 | 0 | 0 |
| 12 | 44 7314 | C | F | 0 | 0 | 0 | 0 | 0 | 0 | 0 | 0 | 0 | 0 | 0 |
| 13 | 44 8295 | H | F | 0 | 0 | 0 | 0 | 0 | 0 | 0 | 0 | 0 | 0 | 0 |
| 14 | 44 9258 | C | F | 0 | 0 | 0 | 0 | 0 | 0 | 0 | 0 | 0 | 0 | 0 |
| 15 | 48 0738 | C | F | 0 | 0 | 0 | 0 | 0 | 0 | 0 | 0 | 0 | 0 | 0 |
| 16 | 48 6153 | H | M | 0 | 0 | 0 | 0 | 0 | 0 | 0 | 0 | 0 | 0 | 0 |
| 17 | 50 1810 | C | M | 0 | 0 | 0 | 0 | 0 | 0 | 0 | 0 | 0 | 0 | 0 |
| 18 | 50 3772 | C | F | 0 | 0 | 0 | 0 | 0 | 0 | 0 | 0 | 0 | 0 | 0 |
| 19 | 50 8924 | C | F | 0 | 0 | 0 | 0 | 0 | 0 | 0 | 0 | 0 | 0 | 0 |
| 20 | 52 3942 | C | F | 0 | 0 | 0 | 0 | 0 | 0 | 0 | 0 | 0 | 0 | 0 |
| 21 | 52 4442 | H | M | 0 | 0 | 0 | 0 | 0 | 0 | 0 | 0 | 0 | 0 | 0 |
| 22 | 54 3239 | C | F | 0 | 0 | 0 | 0 | 0 | 0 | 0 | 0 | 0 | 0 | 0 |
| 23 | 54 3619 | C | F | 0 | 0 | 0 | 0 | 0 | 0 | 0 | 0 | 0 | 0 | 0 |
| 24 | 54 5868 | C | F | 0 | 0 | 0 | 0 | 0 | 0 | 0 | 0 | 0 | 0 | 0 |
| 25 | 54 6257 | C | F | 0 | 0 | 0 | 0 | 0 | 0 | 0 | 0 | 0 | 0 | 0 |
| 26 | 54 6664 | H | F | 0 | 0 | 0 | 0 | 0 | 0 | 0 | 0 | 0 | 0 | 0 |
| 27 | 54 9679 | C | F | 0 | 0 | 0 | 0 | 0 | 0 | 0 | 0 | 0 | 0 | 0 |
| 28 | 56 3379 | C | F | 0 | 0 | 0 | 0 | 0 | 0 | 0 | 0 | 0 | 0 | 0 |
| 29 | 56 3465 | H | F | 0 | 0 | 0 | 0 | 0 | 0 | 0 | 0 | 0 | 0 | 0 |
| 30 | 56 3659 | C | F | 0 | 0 | 0 | 0 | 0 | 0 | 0 | 0 | 0 | 0 | 0 |
| 31 | 56 9114 | C | F | 0 | 0 | 0 | 0 | 0 | 0 | 0 | 0 | 0 | 0 | 0 |
| 32 | 56 9650 | C | F | 0 | 0 | 0 | 0 | 0 | 0 | 0 | 0 | 0 | 0 | 0 |
| 33 | 60 7979 | C | F | 0 | 0 | 0 | 0 | 0 | 0 | 0 | 0 | 0 | 0 | 0 |
| 34 | 62 4302 | C | F | 0 | 0 | 0 | 0 | 0 | 0 | 0 | 0 | 0 | 0 | 0 |
| 35 | 64 4521 | A | F | 0 | 0 | 0 | 0 | 0 | 0 | 0 | 0 | 0 | 0 | 0 |
| 36 | 64 6653 | H | F | 0 | 0 | 0 | 0 | 0 | Dc | Dc | Dc | Dc | Dc | Dc |
| 37 | 64 9034 | C | M | 0 | 0 | 0 | 0 | 0 | 0 | 0 | 0 | 0 | 0 | 0 |
| 38 | 64 9426 | H | F | 0 | 0 | 0 | 0 | 0 | 0 | 0 | 0 | 0 | 0 | 0 |
| 39 | 66 1101 | C | F | 0 | 0 | 0 | 0 | 0 | 0 | 0 | 0 | 0 | 0 | 0 |
| 40 | 66 1649 | C | F | 0 | 0 | 0 | 0 | 0 | 0 | 0 | 0 | 0 | 0 | 0 |
| 41 | 68 5362 | C | M | 0 | 0 | 0 | 0 | 0 | 0 | 0 | 0 | 0 | 0 | 0 |
| 42 | 68 7601 | C | F | 0 | 0 | 0 | 0 | 0 | 0 | 0 | 0 | 0 | 0 | 0 |
| 43 | 74 0600 | C | F | 0 | 0 | 0 | 0 | 0 | 0 | 0 | 0 | 0 | 0 | 0 |
| 44 | 74 8531 | C | M | 0 | 0 | 0 | 0 | 0 | 0 | 0 | 0 | 0 | 0 | 0 |
| 45 | 76 1298 | C | F | 0 | 0 | 0 | 0 | 0 | 0 | 0 | 0 | 0 | 0 | 0 |
| 46 | 76 2719 | C | F | 0 | 0 | 0 | 0 | 0 | 0 | 0 | 0 | 0 | 0 | 0 |
| 47 | 76 7056 | C | F | 0 | 0 | 0 | 0 | 0 | 0 | 0 | 0 | 0 | 0 | 0 |
| 48 | 80 0080 | C | M | 0 | 0 | 0 | 0 | 0 | 0 | 0 | 0 | 0 | 0 | 0 |
| 49 | 80 3313 | C | F | 0 | 0 | 0 | 0 | 0 | 0 | 0 | 0 | 0 | 0 | 0 |
| 50 | 82 4417 | H | M | 0 | 0 | 0 | 0 | 0 | 0 | 0 | 0 | 0 | 0 | 0 |
| 51 | 82 4670 | C | F | 0 | 0 | 0 | 0 | 0 | 0 | 0 | 0 | 0 | 0 | 0 |
| 52 | 90 5388 | C | F | 0 | 0 | 0 | 0 | 0 | 0 | 0 | 0 | 0 | 0 | 0 |

C: Caucasian;
H: Hispanic;
A: Asian;
F: Female;
M: Male;
0: No evidence of any effect;
Dc: Discontinued due to absence of subject on application date

Example 2

Take 1.5 kg of fresh sea grape and 1.5 kg of distilled water, the sea grape used is *Caulerpa lentillifera*, blend and mix thoroughly (temperature is 85° C./time is 30 minutes), followed by filtration using 5-μm and 1-μm filter membranes to give the fluid of sea grape extract (II); the sea grape extract (II) was then subjected to further filtration; the first membrane is the EW membrane made by GE and microfiltration eliminates large particles; the second membrane is the PW membrane made by GE and ultrafiltration eliminates tiny particles; the third membrane is the DK membrane made by GE and nanofiltration eliminates salts; the filtrate is then freeze-dried to give the refined sea grape extract (II). The abovementioned *Caulerpa lentillifera* may be replaced by other species of sea grapes, such as *Caulerpa taxifolia*.

Figure 3:
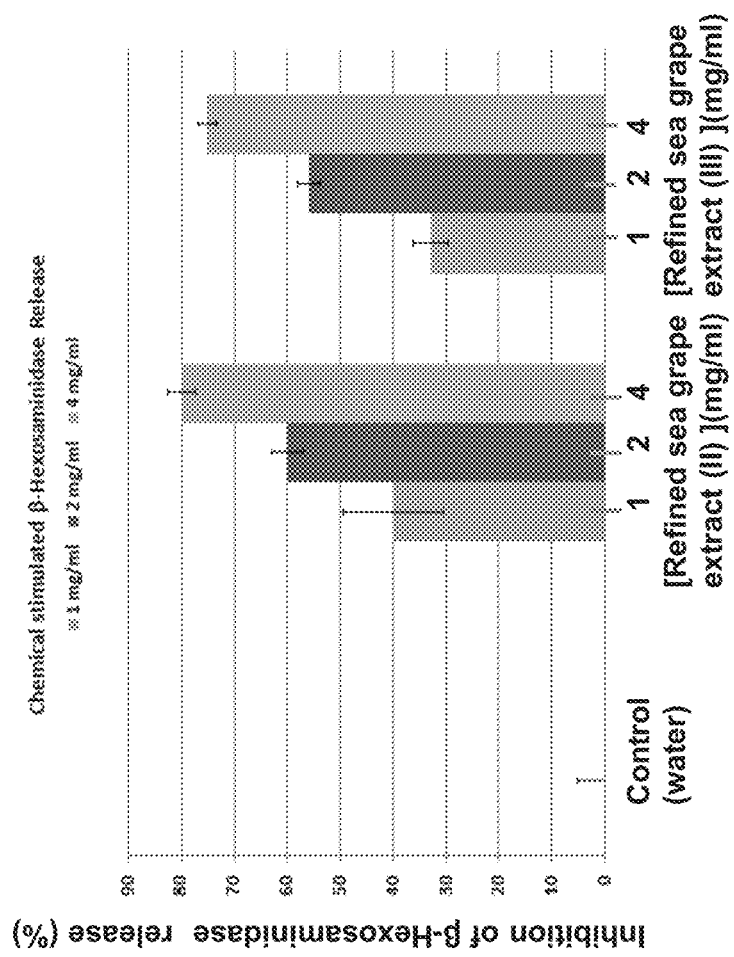
FIG. 3 shows the allergy-inhibiting effect of sea grape extract.

Based on the results of FIG. 3, the refined sea grape extract (II) can inhibit the release of β-hexosaminidase induced by calcium ionophore A23187 (A23187(+) group), 1 mg/ml of the refined sea grape extract (II) can inhibit 40% of β-hexosaminidase release, 2 mg/ml of the refined sea grape extract (II) can inhibit 60% of β-hexosaminidase release, and 4 mg/ml of the refined sea grape extract (II) can inhibit 80% of β-hexosaminidase release.

Example 3

Tale 1.5 kg of fresh sea grape and 1.5 kg of distilled water, the sea grape used is *Caulerpa lentillifera*, blend thoroughly (the temperature is around 25° C./time is around 60 min), followed by filtration by using 5-μm and 1-μm filter membrane to give the sea grape extract (III), the sea grape extract (III) is then subjected to filtration; the first membrane is the EW membrane made by GE and microfiltration eliminates large particles; the second membrane is the PW membrane made by GE and ultrafiltration eliminates tiny particles; the third membrane is the DK membrane made by GE and nanofiltration eliminates salts; the filtrate was then freeze-dried to give the refined sea grape extract (III). The abovementioned *Caulerpa lentillifera* may be replaced by other species of sea grapes, such as *Caulerpa taxifolia*.

Based on the results of FIG. 3, the refined sea grape extract (III) can inhibit the release of β-hexosaminidase induced by calcium ionophore A23187 (A23187(+) group), 1 mg/ml of the refined sea grape extract (III) can inhibit 33% of β-hexosaminidase release, 2 mg/ml of the refined sea grape extract (II) can inhibit 56% of β-hexosaminidase release, 4 mg/ml of the refined sea grape extract (II) can inhibit 75% of β-hexosaminidase release.

What is claimed is:

1. A method of inhibiting allergy by inhibiting the release of β-hexosaminidase comprising administering a composition, wherein the composition comprises an effective amount of a sea grape extract and a cosmetically, edible or pharmaceutically acceptable excipient, wherein the sea grape extract is obtained
   Step 1: blend sea grape in distilled water to make a paste, wherein the weight ratio of sea grape to water is 1:1~20, mix thoroughly to give a sea grape paste;
   Step 2: continuous stirring of the sea grape paste at a stirring temperature of 20~100° C. for 30~120 min;
   Step 3: the fluid obtained after first filtration is the sea grape extract, wherein the sea grape extract comprises allergy-inhibiting activity, wherein the effective amount of the sea grape extract is 1 mg/ml or above.

2. The method according to claim 1, wherein the composition is a cosmetic composition, a food composition, or a pharmaceutical composition.

3. The method according to claim 1, wherein the effect amount of the sea grape extract is 4 mg/ml.

4. The method according to claim 2, wherein the cosmetic composition is selected from the following compositions: creams, multiple emulsions, anhydrous compositions, aqueous dispersions, oils, emulsions, balm, foams, lotions, gels, emulsions, aqueous ethanol solution, hydroglycolic solution, hydrogels, coating poultices, slurries, soaps, shampoo, conditioner, clear slurry, ointment, mousse, hair cream, powders, bars, pencils, sprays, aerosols, capsules, gelatin capsules, soft capsules, hard capsules, tablets, dragees, granules, chewing gum, solutions, suspensions, emulsions, syrups, polysaccharides films, jellies and gelatin.

5. The method according to claim 2, wherein the cosmetic composition may be mixed with products including eye cream, foundation, washing foam (cream), make-up remover, eye shadow, lipstick, lip gloss, lip balm and powder.

6. The method according to claim 4, wherein ingredients of the shampoo are surfactant 10~50%, emollient 0.3~2%, sea grape extract 0.01~0.1%, thickener 0~2%, fragrance 0.1~1%, preservative 0.3~1% and water.

* * * * *